(12) United States Patent
Armbruster et al.

(10) Patent No.: US 9,823,258 B2
(45) Date of Patent: Nov. 21, 2017

(54) IN VITRO DIAGNOSTIC AND PROGNOSIS OF MAJOR ADVERSE EVENTS IN PATIENTS UNDERGOING CORONARY ANGIOGRAPHY

(71) Applicant: Immundiagnostik AG, Bensheim (DE)

(72) Inventors: Franz Paul Armbruster, Bobenheim-Roxheim (DE); Berthold Hocher, Kleinmachnow (DE)

(73) Assignee: Immundiagnostik AG, Bensheim (DE)

( * ) Notice: Subject to any disclaimer, the term of this patent is extended or adjusted under 35 U.S.C. 154(b) by 0 days.

(21) Appl. No.: 15/120,157

(22) PCT Filed: Feb. 20, 2015

(86) PCT No.: PCT/EP2015/053563
§ 371 (c)(1),
(2) Date: Aug. 19, 2016

(87) PCT Pub. No.: WO2015/124707
PCT Pub. Date: Aug. 27, 2015

(65) Prior Publication Data
US 2017/0059584 A1    Mar. 2, 2017

(30) Foreign Application Priority Data

Feb. 20, 2014   (DE) .................. 10 2014 102 224
Feb. 20, 2014   (EP) ..................... 14156042

(51) Int. Cl.
| | | |
|---|---|---|
| G01N 31/00 | (2006.01) | |
| G01N 33/53 | (2006.01) | |
| G01N 33/68 | (2006.01) | |
| G01N 33/70 | (2006.01) | |
| G01N 33/82 | (2006.01) | |

(52) U.S. Cl.
CPC ......... *G01N 33/6893* (2013.01); *G01N 33/70* (2013.01); *G01N 33/82* (2013.01); *G01N 2333/47* (2013.01); *G01N 2333/705* (2013.01); *G01N 2800/347* (2013.01); *G01N 2800/52* (2013.01)

(58) Field of Classification Search
None
See application file for complete search history.

(56) References Cited

U.S. PATENT DOCUMENTS

| | | |
|---|---|---|
| 6,787,660 B1 | 9/2004 | Armbruster et al. |
| 7,851,163 B2 | 12/2010 | Armbruster et al. |
| 7,943,579 B2 | 5/2011 | Armbruster |
| 7,964,363 B2 | 6/2011 | Armbruster et al. |
| 8,133,694 B2 | 3/2012 | Armbruster et al. |
| 9,140,711 B2 | 9/2015 | Armbruster et al. |
| 2007/0087395 A1 | 4/2007 | Armbruster et al. |
| 2011/0003311 A1 | 1/2011 | Armbruster et al. |
| 2012/0156701 A1 | 6/2012 | Anderberg et al. |
| 2013/0316370 A1 | 11/2013 | Anderberg et al. |
| 2014/0038203 A1 | 2/2014 | Arthur et al. |
| 2015/0017738 A1 | 1/2015 | Armbruster et al. |
| 2015/0038411 A1 | 2/2015 | Dschietzig |
| 2016/0025748 A1 | 1/2016 | Armbruster et al. |

FOREIGN PATENT DOCUMENTS

| | | | |
|---|---|---|---|
| KR | 100792630 | 1/2008 | |
| WO | WO 2012/048082 A2 * | 4/2012 | ............. G01N 33/53 |

OTHER PUBLICATIONS

Tian et al. (Experimental and Therapeutic Medicine, Feb. 2014, vol. 7, No. 2, pp. 411-416).*

Xu et al., "Elevated Urinary Level of Vitamin D-binding Protein as a Novel Biomarker for Diabetic Nephropathy," 7 Experimental and Therapeutic Medicine 411 (2014).

* cited by examiner

*Primary Examiner* — Lisa Cook
(74) *Attorney, Agent, or Firm* — James C. Lydon

(57) ABSTRACT

Method of diagnosis and prognosis of contrast media induced nephropathy (CIN) including the steps of i) taking a urine sample from a patient exposed to the application of contrast media, notably patients subjected to coronary angiography; ii) assessing the level of vitamin D binding protein (VDBP) in the urine sample obtained in step (i); iii) relating the urinary vitamin D binding protein level determined in step (ii) to a pre-selected threshold level. A urinary vitamin D binding protein level higher than the pre-selected threshold level indicates that the patient is at risk of renal failure and in need of a dialysis treatment.

8 Claims, 2 Drawing Sheets

IN VITRO DIAGNOSTIC AND PROGNOSIS OF MAJOR ADVERSE EVENTS IN PATIENTS UNDERGOING CORONARY ANGIOGRAPHY

FIELD OF THE INVENTION

The invention relates to in vitro diagnostic means of urine and notably to the determination of urinary vitamin D binding protein.

BACKGROUND OF THE INVENTION

Acute kidney injury (AKI) is a sudden (hours to 7 days) decline of kidney function (Waikar S S et al, *Diagnosis, epidemiology and outcomes of acute kidney injury*. Clin J Am Soc Nephrol, 2008. 3(3): p. 844-61). AKI has become a nosocomial disease with an incidence of 5% to 7% in hospitalized patients in developed countries (Chertow G M et al., *Acute kidney injury, mortality, length of stay, and costs in hospitalized patients*. J Am Soc Nephrol, 2005. 16(11): p. 3365-70; Nash K. et al, *Hospital-acquired renal insufficiency*. Am J Kidney Dis, 2002. 39(5): p. 930-6; Uchino S et al., *Acute renal failure in critically ill patients: a multinational, multicenter study*. Jama, 2005. 294(7): p. 813-8). This incidence appears to be increasing over time (Hsu C Y et al., *Community-based incidence of acute renal failure*. Kidney Int, 2007. 72(2): p. 208-12; Waikar S S et al., *Declining mortality in patients with acute renal failure, 1988 to 2002*. J Am Soc Nephrol, 2006. 17(4): p. 1143-50). AKI is a severe condition associated with a mortality of 45% to 70% (Bagshaw S M et al., *Prognosis for long-term survival and renal recovery in critically ill patients with severe acute renal failure: a population-based study*. Crit Care, 2005. 9(6): p. R700-9; Liangos O et al., *Epidemiology and outcomes of acute renal failure in hospitalized patients: a national survey*. Clin J Am Soc Nephrol, 2006. 1(1): p. 43-51; Mehta R L et al, *Acute renal failure definitions and classification: time for change?* J Am Soc Nephrol, 2003. 14(8): p. 2178-87; Basile D P et al, *Pathophysiology of acute kidney injury*. Compr Physiol. 2(2): p. 1303-53]. In addition to increased mortality, AKI is associated with a significant prolongation of hospital stay and high financial costs [Lattanzio M R et al, *Acute kidney injury: new concepts in definition, diagnosis, pathophysiology, and treatment*. J Am Osteopath Assoc, 2009. 109(1): p. 13-9].

Renal pathology is the most frequent cause of AKI and accounts for 35% to 70% of AKI cases [Brivet F G et al., *Acute renal failure in intensive care units—causes, outcome, and prognostic factors of hospital mortality; a prospective, multicenter study. French Study Group on Acute Renal Failure*. Crit Care Med, 1996. 24(2): p. 192-8; Liano F et al, *Epidemiology of acute renal failure: a prospective, multicenter, community-based study*. Madrid Acute Renal Failure Study Group. Kidney Int, 1996. 50(3): p. 811-8.]. Ischemic or nephrotoxic injury of the kidney with subsequent acute tubular necrosis (ATN) causes 80% to 90% of AKI due to renal aetiology (Liano F et al., *The spectrum of acute renal failure in the intensive care unit compared with that seen in other settings*. The Madrid Acute Renal Failure Study Group. Kidney Int Suppl, 1998. 66: p. S16-24).

During AKI, increased urinary excretion of biomarkers may be the result of both tubular secretion and defective proximal tubule reabsorption due to megalin dysfunction (Kuwabara T et al., *Urinary neutrophil gelatinase-associated lipocalin levels reflect damage to glomeruli, proximal tubules, and distal nephrons*. Kidney Int, 2009. 75(3): p. 285-94; Wagener G et al., *Increased incidence of acute kidney injury with aprotinin use during cardiac surgery detected with urinary NGAL*. Am J Nephrol, 2008. 28(4): p. 576-82; Mahadevappa R et al., *Megalin in acute kidney injury—foe and friend*. Am J Physiol Renal Physiol. 2013: p. 6). In AKI some biomarkers, such as L-FABP and NGAL, are secreted by tubular cells into the urine; however, these are also present in increased amounts in plasma during AKI (Mishra J et al., *Neutrophil gelatinase-associated lipocalin (NGAL)as a biomarker for acute renal injury after cardiac surgery*. Lancet, 2005. 365(9466): p. 1231-8). Furthermore, contrast media cause increased vasoconstriction and decreased vasodilatation in the renal medulla, leading to hypoxia and even acute tubular necrosis known as contrast-induced nephropathy (CIN) that tends to occur especially often in diabetics and patients with preexisting renal insufficiency (Wong P C et al., *Pathophysiology of contrast-induced nephropathy*. Int J Cardiol. 158(2): p. 186-92).

While there are know biomarkers that correlate with progression of the disease, there are no such biomarkers available which are predictive for life threatening complications and mortality caused by contrast media. Applying new technologies of genomic analysis (e.g., RNA subtraction or DNA microarrays) and proteomic approaches to identify novel proteins that encode for renal injury are ongoing but not available. Thus, the state of the art represents a problem.

SUMMARY OF THE INVENTION

This problem is solved by a in-vitro diagnostic method as claimed in claim 1. Preferred embodiments are disclosed in the dependent claims.

The present application refers to a method of diagnosis of contrast media induced nephropathy (CIN) comprising the steps of i) taking a urine sample from a patient exposed to the application of contrast media, notably patients subjected to coronary angiography; ii) assessing the level of vitamin D binding protein (VDBP) in the urine sample obtained in step (i); iii) relating the urinary vitamin D binding protein level determined in step (ii) to a pre-selected threshold level, wherein a urinary vitamin D binding level higher than said pre-selected threshold level indicates that the patient is at risk of renal failure and in need of a dialysis treatment. In a preferred embodiment, said method of diagnosis of contrast media induced nephropathy as claimed in claim 1, further comprises the steps of further assessing the level of creatinine in the urine sample obtained in step (i); calculating the ratio of urinary VDBP to urinary creatinine (uCr) and relating it to a pre-selected threshold level, wherein an increased VDBP/uCr ratio indicates that the patient is at risk of renal failure and in need of a dialysis treatment.

In another embodiment, the urine sample may be taken from patient a with pre-existing renal impairment and/or exposed to contrast media; and relating the urinary VDBP level to a renoprotective therapy. This embodiment may further comprise a a measurement of urinary creatinine in the same and calculating the ratio of urinary VDBP to urinary creatinine. The present application refers to using the level of urinary VDBP or the ratio urinary VDBP/uCr as a predictor of major adverse renal events (MARE). Consequently, the level of urinary VDBP may be a biomarker for preclinical trials for patients with renal impairment or heart failure.

Further embodiments of the invention encompass a determination of KIM-1 and/or GFR (glomerular filtration rate).

The urinary VDBP level is preferably assessed by lateral flow immunochromatography or enzyme-linked immunosorbent assay.

Further features, embodiments and advantages of the present invention will be set forth in or become apparent from the detailed description of the invention, the representative examples and embodiments of the invention and the drawings which follow. The given examples shall not be construed a limitation to the scope of protection as defined in the attached claims.

DETAILED DESCRIPTION OF THE INVENTION

Contrast media induced nephropathy (CIN) is associated with increased morbidity and mortality. The inventors therefore examined 330 patients with diabetes mellitus or mild renal impairment who were subjected to coronary angiography. Blood was collected from those patients before and 24 hours after the contrast media application. The patients were then followed for 90 days for the composite endpoint major adverse renal events—MARE (MARE: need for dialysis, doubling of serum creatinine after 90 days, unplanned emergency rehospitalization or death).

It was found that urinary VDBP concentrations 24 hours after contrast media exposure were predictive for a need for dialysis (no dialysis: 423.8 ng/ml; n=319; need for dialysis; 1006.0091 ng/ml, n=11; p<0.001), death (no death during follow-up: 334.7, n=322; death during follow-up; 401.3 ng/ml, n=8; p<0.003) and the composite endpoint MARE (no MARE: 367.0 ng/ml, n=314; MARE; 733.4 ng/ml, n=16; p<0.001) during the follow-up of 90 days after contrast media exposure. When corrected for urinary creatinine concentrations, results remain significant with similar significance levels. Thus, the measurement of urinary VDBP proved to be a powerful 90 day biomarker after contrast media exposure due to coronary angiography and its measurement is a powerful tool for the development of drugs against acute renal failure/CIN.

Figure 1:
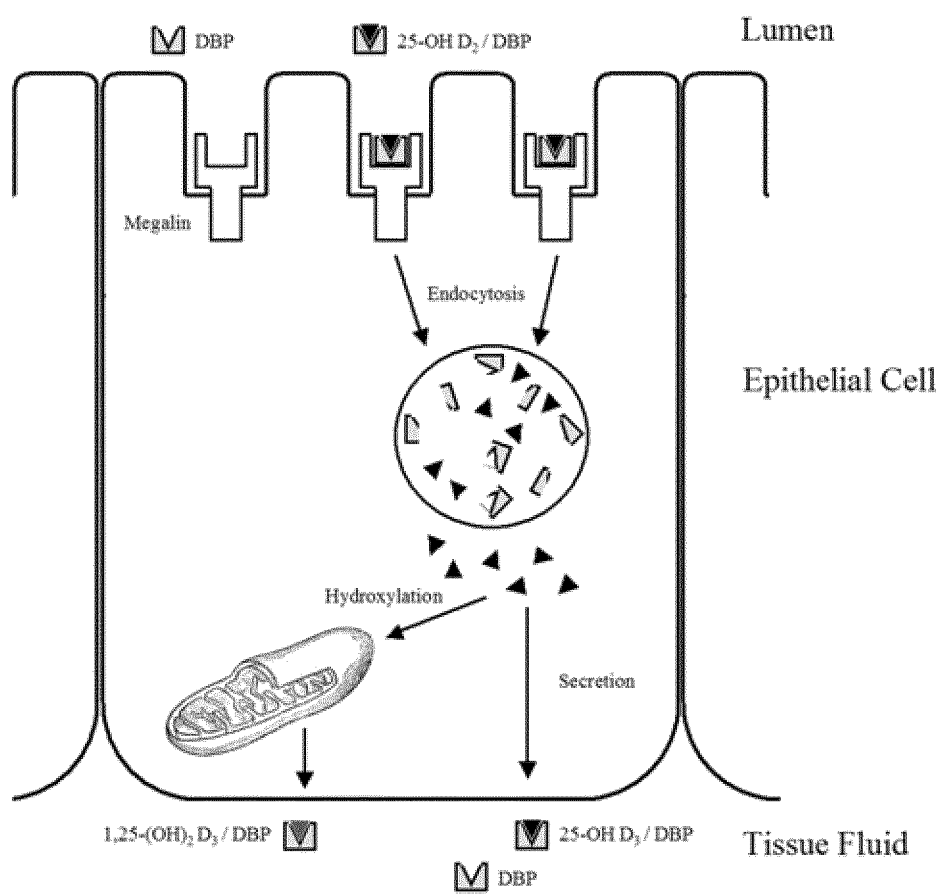
FIG. 1 is a schematic drawing of the megalin function in renal uptake and activation of 25-(OH) Vitamin-D as described Nykjaer, A., et al. in *An endocytic pathway essential for renal uptake and activation of the steroid 25-(OH) vitamin D*3. Cell, 1999. 96(4): p. 507-15

Without wishing to be bound by a theory, vitamin-D-binding protein (VDBP) is a low molecular weight protein that is filtered through the glomerulus in a complex with 25-(OH)-vitamin D. The complex of 25-(OH) vitamin D and VDBP is uptaken by megalin in the brush border of proximal tubule cells. In the normal kidney VDBP is reabsorbed by megalin-mediated endocytosis and catabolized by proximal tubule epithelial cells reducing the urinary excretion to trace amounts (Mahadevappa, R., et al., *Megalin in acute kidney injury—foe and friend*. Am J Physiol Renal Physiol. 2013: p. 6.). However, if tubular cells are damaged like it happens during CIN, the tubular cell specific megalin mediated reabsorption of VDBP may be absent, since tubular cells are dysfunctional or dying. More precisely, the carrier VDBP is degraded in lysosomes, while 25-(OH) vitamin D is converted into 1,25-dihydroxy vitamin D and resecreted into the circulation (FIG. 1). Acute tubular necrosis (ATN) occurs already during the renal tubular epithelial cell injury when renal blood flow decreases to a level resulting in severe cellular ATP depletion that in turn leads to acute cell injury and dysfunction. Since receptor-mediated uptake of VDBP is energy-consuming, tubular injury is expected to result in urinary VDBP loss (Doorenbos C R et al., *Possible renoprotection by vitamin D in chronic renal disease: beyond mineral metabolism*. Nat Rev Nephrol, 2009. 5(12): p. 691-700). While glomerular filtration rate (GFR) decrease can be diagnosed only hours after renal insult, increased VDBP concentration may be detected as early as ATN occurs. Whether VDBP is related to acute tubulointerstitial damage and long term prognosis of the kidney injury has not yet specifically been addressed. Notwithstanding, urinary VDBP may serve as a biomarker of an acute renal damage and urinary VDBP increases with increasing severity of renal damage and responds to renoprotective therapy. The urinary VDBP level is therefore a potential predictor of adverse events such as death, initiation of dialysis, doubling of serum creatinine, non-elective hospitalization, 25% decrease of the GFR and development of contrast induced nephropathy (CIN) during the 3 months follow-up.

The biomarker role of urinary VDBP is also unique, suggesting a new physiological mechanism, compared with established tubular damage markers Kidney Injury Molecule-1 (KIM-1), VDBP/urinary creatinine (VDBP/uCr) and KIM-1/urinary creatinine (KIM-1/uCr) ratio in the cohort of patients with preexisting renal impairment, i.e. patients with plasma creatinine of at least 1.1 mg/dl or preexisting diabetes mellitus.

EXAMPLES

Example 1 Course of the Study

The prospective cohort study on 327 consecutive patients with coronary angiography was performed between January 2010 and December 2011 in the Department of Cardiology of the Charité—Universitätsmedizin Berlin. The study was conducted according to the Declaration of Helsinki, the European Guidelines on Good Clinical Practice, and relevant national and regional authority requirements and ethics committees. Informed consent was obtained from each participant prior to involvement into the study. Inclusion criteria: Consecutive patients with plasma creatinine of at least 1.1 mg/dl or preexisting diabetes mellitus were enrolled in the study. Exclusion criteria: Patients with end-stage renal disease as well as patients who did not sign an informative consent were excluded from the study.

Figure 2:
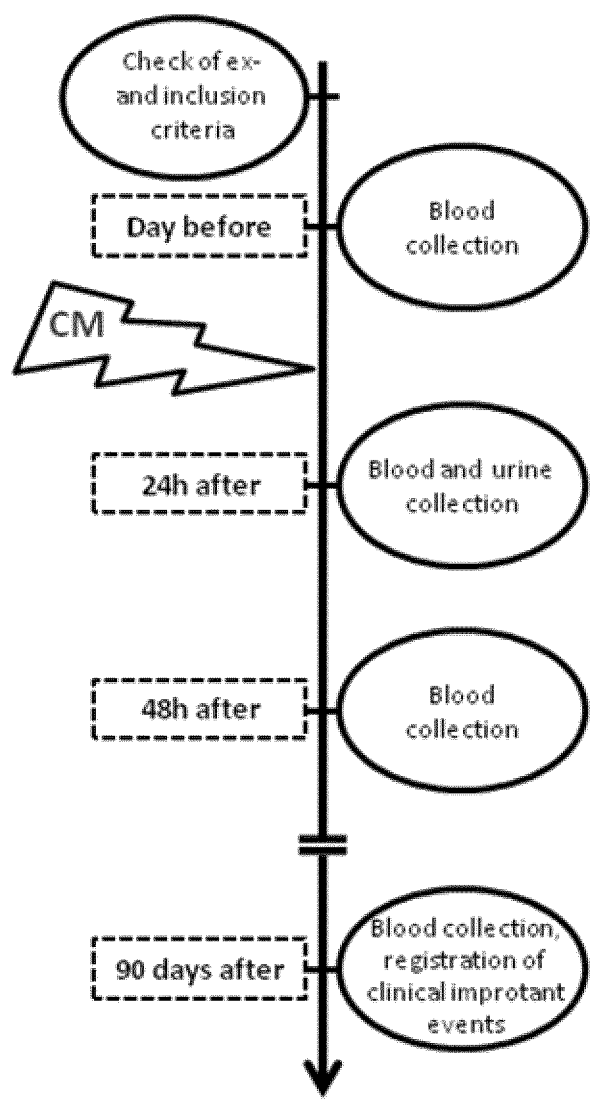
FIG. 2 is a schematic drawing and timeline of the study leading to the invention as claimed.

Referring to FIG. 2, after enrollment into the study, patients underwent first blood- and urine sampling for obtaining basal values. As next, paraclinical examination with contrast media was performed. In the present study, only water-soluble, non-ionic, monomeric, low-osmolar, iodine-based contrast agent Iobitridol was used in a concentration of 350 mg Jod/ml (XENETIX® 350, Guerbet GmbH, Sulzbach/Taunus, Germany). Further, blood- and urine samples were obtained 24 and 48 hrs., and finally 3 months after contrast agent infusion.

Study endpoints were death, initiation of dialysis, doubling of serum creatinine, non-elective hospitalization and 25% decrease of the glomerular filtration rate (GFR) during the 3 months follow-up. Additionally, incidences of contrast induced nephropathy (CIN) and major adverse renal event (MARE) were assessed. CIN was defined as an increase of creatinine of 25% or 0.5 mg/dl from the baseline within 48 hours. MARE was defined as an occurrence of death, initiation of dialysis or a doubling of the creatinine at follow-up.

The statistical analysis was made using SPSS 20 (IBM® SPSS® Statistics IBM Cooperation, Armonk, USA). Differences among the biomarkers were estimated with Mann-Whitney-U-Test for independent or Wilcox on-test for dependent variables. For all analyses a two-sided p<0.05 was considered statistically significant.

Example 2 Sample Treatment And Measurement

The samples were frozen at −80° C. the very same day. Before freezing, blood samples were centrifuged 5 minutes with 3000 rotates per minutes and only the plasma was frozen. Creatinine was measured according to the method of Jaffé. GFR was estimated according to the modification of diet in renal disease (MDRD) formula. Cystatin C was measured by an immunonephelometric method using polystyrene particles coated with human cystatin c specific antibodies (Siemens Healthcare Diagnostics Products GmbH, Marburg, Germany).

Human VDBP was measured with a commercially available sandwich ELISA (Immundiagnostik, catalog # K2314, Bensheim, Germany), according to the manufacturer's instructions. Briefly, plasma (diluted 1:40000) or urine (diluted 1:2-1:5 for controls and 1:10-1:3000 for the other groups depending on the concentration of VDBP) was incubated in a microtiter plate coated with polyclonal anti-VDBP antibodies for one hour. Subsequently, a polyclonal peroxidase-labeled rabbit-anti-VDBP detection antibody was added and incubated for one hour. After washing, tetramethylbenzidine was added as substrate for 15 minutes. After adding a stop solution, absorbance at 450 nm was measured by a spectrophotometer (BenchMark Plus, Bio-Rad Laboratories, Veenendaal, The Netherlands). Using a standard curve generated with VDBP protein as provided by the manufacturer, final VDBP concentrations were calculated. The detection limit of this ELISA is 1.23 ng/ml; intra-assay CV<5.0% for 16 replicate determinations at concentrations of 24.2 and 42.9 mg/dl and inter-assay CV<12.7% for a concentration of 19.3 mg/dl in 14 different assays on two different lots; recovery ranges from 85-116% and linearity was acceptable ($r2=0.998$). Rat VDBP was measured using another commercially available ELISA kit (Alpco, Salem, N.H.), according to the manufacturer's instructions. Detection limit as provided by manufacturer: 3.125 ng/ml, range 3.125-100 ng/ml. VDBP excretion was calculated from the VDBP concentration in urine collected over a 24-hour period (Mirkovic, K., et al., Urinary vitamin D binding protein: a potential novel marker of renal interstitial inflammation and fibrosis. PLoS One. 8(2): p. e55887).

For the measurement of Kidney Injury Molecule-1 (KIM-1) in urine, KIM-1 ELISA TEST KIT for the detection of KIM-1 in human (BioAssay Works®, L.L.C., Ijamsville, USA) was used according to manufacturer instruction (Vaidya V S et al., A rapid urine test for early detection of kidney injury. Kidney Int, 2009. 76(1): p. 108-14) Kim-1 antigen detection levels in urine greater than 800 pg/ml were realized with a dose-response relationship covering a three-log range.

Example 3—Analysis

Patients characteristics. A total of 327 consecutive patients underwent coronary angiography (239 (76.1%) men and 75 (23.9%) women) with a median age of 68.89±9.69 years and a body mass index (BMI) of 28.99±5.44 kg/m² were enrolled in the study. 169 (53.8%) patients were previously diagnosed with diabetes mellitus, 81 (25.8%) suffered congestive heart failure and 86 (27.4%) had an anemia. The mean volume of injected contrast medium was 112.33±55.24 ml. The means of urinary VDBP and KIM-1 of the entire cohort at study entry were 12.80±3515.23 and 0.161±0.19 respectively. In addition, VDBP/urinary Creatinine (VDBP/uCr) and KIM-1/urinary Creatinine (KIM-1/uCr) ratio as well as GFR were calculated, and were at baseline 1.72±1008.42; 0.026±0.02 and 64.06±21.05 respectively (Table 1).

TABLE 1

Patients characteristics at baseline

| Patients characteristics | N | 314 |
|---|---|---|
| Female (%)/male (%) | | 75 (23.9%)/239 (76.1%) |
| Age (ME ± SD) | Years | 68.89 (±9.69) |
| Body mass index (ME ± SD) | kg/m² | 28.99 (±5.44) |
| CM-volume (ME ± SD) | Ml | 112.33 (±55.24) |
| Baseline plasma creatinine (ME ± SD) | mg/dl | 1.24 (±0.43) |
| Baseline GFR (ME ± SD) | ml/min/1.73 m² | 64.06 (±21.05) |
| Diabetes mellitus (%) | | 169 (53.8%) |
| Congestive heart failure (%) | | 81 (25.8%) |
| Anemia (%) | | 86 (27.4%) |

CM: contrast media,
VDBP: vitamin D binding protein,
KIM-1: kidney injury molecule 1,
uCr: urinary creatinine,
CIN: contrast induced nephropathy,
GFR: glomerular filtration rate estimated with the MDRD formula,
ME: mean,
M: median,
SD: standard deviation Example 4—Comparison and Correlation Between VDBP and Kim-1 and the Study Endpoints Eight patients died during the follow-up time of 90 days. Death occurred at a median of 74.5 (7-95) days after study entry. The causes of death were cardiovascular diseases in 4 patients, infections in 2 patients, respiratory failure in 1 patient and other/unknown reasons in 1 patient; see Table 2 below.

TABLE 2

Time to death and causes of death during the follow up

| Patient ID | Days from the inclusion into the study to death | Cause of death |
|---|---|---|
| 19 | 7 | Unknown |
| 29 | 90 | Bradyarrhythmia with asystole |
| 42 | 84 | Respiratory failure |
| 124 | 79 | Acute decompensated heart failure |
| 133 | 26 | Sepsis |
| 149 | 95 | Sudden cardiac death |
| 164 | 70 | Sepsis and infective endocarditis |
| 276 | 48 | Acute pulmonary embolism with acute decompensated heart failure |

Median VDBP levels were significantly lower in survivors (12.7±2650.5 ng/ml) compared with deceased patients (188.0±520.4 ng/ml; p=0.003). Calculated VDBP/uCr ratio confirmed this significant difference as it was 1.71±349.0 ng/ml/mmol/l in patients that stayed alive at the end of the follow-up compared to 16.45±286.2 ng/ml/mmol/l in those who did not survive (p=0.004). Urinary KIM-1 and KIM-1/uCr did not differ between survivors vs non survivors 24 hrs. after CM injection; see Table 3 below:

TABLE 3

Correlation between urinary concentration of VDBP and KIM-1 24 hrs after CM injection and the occurrence of the study enpoints

| | | VDBP | | | KIM-1 | | |
|---|---|---|---|---|---|---|---|
| | | M | SD | p | M | SD | p |
| Whole cohort | | 12.8 | 3515.2 | | 0.16 | 0.192 | |
| CIN | No | 11.5 | 3793.6 | 0.032 | 0.16 | 0.195 | 0.912 |
| | Yes | 29.5 | 1326.7 | | 0.19 | 0.119 | |
| Death | Alive | 12.7 | 2650.5 | 0.003 | 0.16 | 0.191 | 0.181 |
| | Dead | 188.0 | 520.4 | | 0.22 | 0.230 | |
| Dialysis | No | 12.6 | 2640.0 | <0.001 | 0.16 | 0.189 | 0.382 |
| | Yes | 125.7 | 1796.6 | | 0.21 | 0.350 | |
| Non-elective hospitalization | No | 12.3 | 2853.3 | 0.140 | 0.16 | 0.186 | 0.729 |
| | Yes | 19.7 | 453.4 | | 0.15 | 0.256 | |
| MARE | No | 11.4 | 2961.1 | <0.001 | 0.16 | 0.175 | 0.146 |
| | Yes | 107.5 | 1526.6 | | 0.22 | 0.321 | |
| 25% decrease of GFR (90 days) | No | 11.6 | 3055.2 | 0.624 | 0.16 | 0.183 | 0.032 |
| | Yes | 12.3 | 29.8 | | 0.13 | 0.248 | |

VDBP: vitamin D binding protein,
KIM-1: kidney injury molecule 1,
CIN: contrast induced nephropathy,
MARE: major adverse renal event,
GFR: glomerulary filtration rate estimated with the MDRD formula,
N: number of patients,
M: median,
SD: standard deviation,
p: significance according to Mann-Whitney-U-test Impairment of a kidney function measured by 25% decrease of GFR was detected in 19 patients. It significantly correlated only with increased urinary KIM-1 (0.16±0.183 ml/min/1.73 $m^2$ vs 0.13±0.248 ml/min/1.73 $m^2$, p=0.032). CIN was diagnosed in 21 patients of our study population. VDBP as well as VDBP/uCr 24 hrs after CM injection were significantly higher in patients with CIN (29.5±1326.7 ng/ml and 2.64±185.9 ng/ml/mmol/l vs 11.5±3793.6 ng/ml and 1.65±1096.5 ng/ml/mmol/l respectively).

11 patients in the cohort had to undergo dialysis during the follow-up period. VDBP as well as VDBP/uCr 24 hrs after CM injection were significant predictors of dialysis need, as their values were significantly higher in patients needed dialysis treatment subsequently (125.7±1796.6 ng/ml and 37.0±345.2 ng/ml/mmol/l vs 12.6±2640.0 ng/ml and 1.69±345.6 ng/ml/mmol/l respectively). Only increased urinary KIM-1/uCr but not urinary KIM-1 alone significantly predicted subsequent dialysis need (0.04±0.039 ng/ml/mmol/l vs 0.03±0.020 ng/ml/mmol/l; p=0.001).

TABLE 4

Correlation between VDBP/uCr and KIM-1/uCr 24 hrs after CM injection and the occurrence of the study endpoints

| | | VDBP/uCr | | | KIM-1/uCr | | |
|---|---|---|---|---|---|---|---|
| | | M | SD | p | M | SD | p |
| Whole cohort | | 1.72 | 1008.4 | | 0.03 | 0.022 | |
| CIN | No | 1.65 | 1096.5 | 0.038 | 0.03 | 0.024 | 0.534 |
| | Yes | 2.64 | 185.9 | | 0.03 | 0.016 | |
| Death | Alive | 1.71 | 349.0 | 0.004 | 0.03 | 0.022 | 0.121 |
| | Dead | 16.45 | 286.2 | | 0.04 | 0.039 | |
| Dialysis | No | 1.69 | 345.6 | <0.001 | 0.03 | 0.020 | 0.001 |

TABLE 4-continued

Correlation between VDBP/uCr and KIM-1/uCr 24 hrs after CM injection and the occurrence of the study endpoints

| | | VDBP/uCr | | | KIM-1/uCr | | |
|---|---|---|---|---|---|---|---|
| | | M | SD | p | M | SD | p |
| | Yes | 37.00 | 345.2 | | 0.04 | 0.052 | |
| Non-elective hospitalization | No | 1.54 | 377.0 | 0.046 | 0.02 | 0.021 | 0.014 |
| | Yes | 3.32 | 119.0 | | 0.03 | 0.031 | |
| MARE | No | 1.40 | 387.3 | <0.001 | 0.02 | 0.020 | 0.002 |
| | Yes | 16.45 | 301.8 | | 0.04 | 0.047 | |
| 25% decrease of GFR (90 days) | No | 1.53 | 401.9 | 0.985 | 0.02 | 0.020 | 0.526 |
| | Yes | 2.23 | 10.0 | | 0.03 | 0.041 | |

VDBP: vitamin D binding protein,
KIM-1: kidney injury molecule 1,
uCr: urinary creatinine,
CIN: contrast induced nephropathy,
MARE: major adverse renal event,
GFR: glomerulary filtration rate estimated with the MDRD formula,
N: number of patients,
M: median,
SD: standard deviation,
p: significance according to Mann-Whitney-U-test Cumulative occurrence of the major adverse renal events (MARE) defined as an occurrence of death, initiation of dialysis or a doubling of serum creatinine at follow-up seeing in 16 patients of our study population was predicted by significantly higher levels of VDBP as well as VDBP/uCr as early as 24 hrs. after CM injection (107.5±1526.6 ng/ml and 16.45±301.8 ng/ml/mmol/l vs 11.4±2961.1 ng/ml and 1.40±387.3 ng/ml/mmol/l respectively). Increased urinary KIM-1/uCr ratio but not urinary KIM-1 alone was a predictor of MARE (0.04±0.047 ng/ml/mmol/l vs 0.02±0.020 ng/ml/mmol/l; p=0.002).

TABLE 5

Significance of measured biomarkers as predictors of renal events

| | VDBP | VDBP/uCr ratio | KIM-1 | KIM-1/uCr ratio |
|---|---|---|---|---|
| CIN | + | + | | |
| Death | ++ | ++ | | |
| Dialysis | +++ | +++ | | ++ |
| Hospitalization | | + | | + |
| MARE | +++ | +++ | + | ++ |
| 25% decrease of GFR (90 days) | | | + | |

VDBP: vitamin D binding protein,
KIM-1: kidney injury molecule 1,
uCr: urinary creatinine,
CIN: contrast induced nephropathy,
MARE: major adverse renal event,
GFR: glomerulary filtration rate,
+: significant with p < 0.05,
++: significant with p < 0.01,
+++: significant with p < 0.001

In addition, we assessed correlation between non-elective hospitalization during the 90 days follow-up and urinary VDBD, urinary KIM-1, VDBP/uCr and KIM-1/uCr. Statistical analysis revealed that levels of VDBP/uCr 24 hrs after CM injection were significantly higher in patients needed non-elective hospitalization during the 90 days follow-up (3.32±119.0 ng/ml/mmol/l vs 1.54±377.0 ng/ml/mmol/l; p=0.046). This correlation was true also for KIM-1/uCr ratio (0.03±0.031 ng/ml/mmol/l vs 0.02±0.021 ng/ml/mmol/l; p=0.014).

The study therefore demonstrates that urinary VDBP is a biomarker of contrast medium induced tubulointerstitial damage, independent of GFR and KIM-1, in patients with preexisting renal impairment. VDBP and VDBP/uCr were strong predictors of death, dialysis, CIN and MARE, and therefore performed better than KIM-1/uCr ratio, that could predict only dialysis and MARE and also better then KIM-1 alone that was significantly associated only with 25% decrease of GFR during 90 days of follow-up. In addition, VDBP/uCr and KIM-1/uCr were significantly associated with non elective hospitalization during the follow-up (Table 5).

The results are consistent with previous reports on the urinary loss of VDBP in the setting of renal damage in a rat adriamycin-induced nephrotoxicity model (Malard V et al., *Urine proteomic profiling of uranium nephrotoxicity*. Biochim Biophys Acta, 2009. 1794(6): p. 882-91) as well as in the setting of chronic kidney disease in humans (Thrailkill K M et al., *Enhanced excretion of vitamin D binding protein in type 1 diabetes: a role in vitamin D deficiency?* J Clin Endocrinol Metab. 96(1): p. 142-9; Doorenbos C R et al., *Antiproteinuric treatment reduces urinary loss of vitamin D-binding protein but does not affect vitamin D status in patients with chronic kidney disease*. J Steroid Biochem Mol Biol. 128(1-2): p. 56-61). Interestingly, urinary VDBP as well as urinary KIM-1 (van Timmeren M M et al., *Tubular kidney injury molecule-1 (KIM-1) in human renal disease*. J Pathol, 2007. 212(2): p. 209-17) were associated with interstitial inflammation independently of albuminuria, rendering VDBP an even more interesting candidate biomarker.

It has previously been shown that urinary VDBP increased with increasing severity of renal damage, and responded to renoprotective therapy, but remained 100-fold increased as compared to healthy normoalbuminuric subjects. In addition, urinary VDBP is about 4-fold increased in diabetic patients with normoalbuminuria. These facts suggest that tubulointerstitial damage, considered the final common pathway towards end-stage renal disease (ESRD), are present at the early asymptomatic stage and persist to a considerable extent despite current best available medical treatment. Indeed, urinary VDBP was strongly and consistently elevated in rats with adriamycin-induced nephropathy on a very early stage, before prefibrotic biomarkers could even be detected. In addition, increased urinary VDBP was strongly associated with markers of tubulointerstitial fibrosis after induction of nephrosis, suggesting that not only protein overload of the megalin complex plays a role in urinary VDBP loss, but also damaged tubular epithelial cells in areas of tubulointerstitial fibrosis loss their ability to handle receptor-mediated endocytosis of VDBP, resulting in increased urinary excretion of VDBP.

Increased level of urinary VDBP proved in our study as a predictor of all cause mortality. To our best knowledge, there are no data on association between urinary VDBP and mortality in the up to date literature. Nevertheless, in a number of studies, vitamin D plasma concentrations was associated with higher mortality rates (Leaf D E et al., *Dysregulated mineral metabolism in patients with acute kidney injury and risk of adverse outcomes*. Clin Endocrinol (Oxf). 79(4): p. 491-8; Trummer O et al., *Vitamin D and mortality: a Mendelian randomization study*. Clin Chem. 59(5): p. 793-7).

KIM-1 is a superfamily of immunoglobulin transmembrane receptors that is expressed in the tubules in the setting of kidney injury and facilitates the removal of apoptotic and necrotic bodies. The US Food and Drug Administration approved KIM-1 as a one of the of urinary biomarkers in a panel for preclinical trials. Nevertheless, recent clinical trial on a cohort of 700 adult critically ill patients reported that urinary KIM-1 can only predict acute kidney injury at the same time when the rise in serum creatinine levels occurred for the first time (de Geus, H. R., et al., *Time of injury affects urinary biomarker predictive values for acute kidney injury in critically ill, non-septic patients*. BMC Nephrol. 14(1): p. 273). These data are in line with our results which show a correlation between increase of urinary KIM-1 and 25% decrease of GFR. A number of studies reported even that urinary KIM-1 was not significantly associated with acute kidney injury in adults or children (Parikh, C. R., et al., *Performance of kidney injury molecule-1 and liver fatty acid-binding protein and combined biomarkers of AKI after cardiac surgery*. Clin J Am Soc Nephrol. 8(7): p. 1079-88; Kwon, S. H., et al., *KIM-1 expression predicts renal outcomes in IgA nephropathy*. Clin Exp Nephrol. 17(3): p. 359-64). Verbrugge et al. show in their study on patients with acute decompensated heart failure that urinary KIM-1 is no reliable predictor of persistent renal impairment or all-cause mortality. At the same time, the ratio KIM-1/uCr may be of value for the detection of renal injury.

Given the pitfalls of reporting absolute concentrations of urinary biomarkers, such as oliguria causing an increase in the absolute concentration of a biomarker, and polyuria as a reason of its decrease, normalizing a urinary biomarker concentration to urinary creatinine takes into account differences in urinary flow rate. However, when normalizing, the rate of creatinine excretion by the kidney has also to be taken into consideration. Under non stable conditions, such as acute kidney failure, urinary creatinine excretion changes over time. If the assessed biomarker behaves exactly like creatinine in terms of filtration, secretion and reabsorption (Waikar S S et al., *Normalization of urinary biomarkers to creatinine during changes in glomerular filtration rate*. Kidney Int. 78(5): p. 486-94), the normalized level will be affected by differences in urinary creatinine excretion, as it was seeing in our results comparing predictive values of VDBP and KIM-1 alone vs VDBP/uCr and KIM-1/uCr.

In summary, urinary VDBP and VDBP/uCr were proven being powerful 90 day outcome biomarkers after contrast media exposure, e.g. due to coronary angiography, and are thus useful tools for the development of drugs against acute renal failure/CIN. Urinary KIM-1/uCr is further a good predictor of major adverse renal event and dialysis.

The invention claimed is:
1. A method for diagnosis of contrast media induced nephropathy (CIN) and prognosis of acute kidney injury (AKI) comprising the steps of
  i) taking a first urine sample from a patient scheduled to undergo coronary angiography comprising administration of a contrast media agent;
  ii) taking a second urine sample from said patient no later than 24 hours after said patient has undergone said coronary angiography;
  iii) taking a third urine sample from said patient no later than 48 hours after said patient has undergone said coronary angiography;
  iv) comparing the levels of creatinine in said first and third urine samples to diagnose whether nephropathy was caused by said contrast media agent;
  v) assessing the level of vitamin D binding protein (VDBP) in said second urine sample,
  vi) calculating a ratio of urinary VDBP to urinary creatinine (uCr) in said second urine sample and comparing it to a pre-selected threshold level, vii) predicting whether said patient will suffer acute kidney injury within a 90 day period following said coronary angiography based on whether said VDBP level in said second urine sample is higher than a pre-selected VDBP threshold level or whether the VDBP/uCr ratio in said second urine sample is higher than a pre-selected VDBP/uCr threshold value.

2. The method of claim 1, wherein contrast media induced necropathy is defined as an increase of creatinine in said third urine sample of either 25% in comparison to the creatinine level in said first urine sample or 0.5 mg/dl creatinine in said third urine sample.

3. The method of claim 1, wherein said patient has a pre-existing renal impairment.

4. A method for monitoring a renoprotective therapy, including the method of claim 1, in which the level of VDBP or the ratio VDBP/uCr is used as a predictor of a major adverse renal event selected from the group consisting of death, initiation of dialysis or a doubling of creatinine level in the patient's urine within said 90 day period.

5. The method of claim 1, wherein the level of urinary VDBP is used as a biomarker in a preclinical trial for patients with renal impairment or heart failure.

6. The method of claim 1, further comprising
determining a level of Kidney Injury Molecule-1 and/or a glomerular filtration rate in at least one of said first, second and third urine samples.

7. The method of claim 1, wherein the urinary VDBP level is assessed by lateral flow immunochromatography.

8. The method of claim 1, wherein the level of vitamin D binding protein (VDBP) in said second sample is assessed by an enzyme-linked immunosorbent assay.

* * * * *